US009855219B2

(12) United States Patent
Arfsten et al.

(10) Patent No.: US 9,855,219 B2
(45) Date of Patent: Jan. 2, 2018

(54) CORE-SHELL NANOPARTICLES

(75) Inventors: Nanning Joerg Arfsten, Aachen (DE);
Steven Armes, Sheffield (GB); Pascal Jozef Paul Buskens, Heerlen (NL);
Jens Christoph Thies, Eijsden (NL);
Patrick Wilhelmus Antonius Vrijaldenhoven, Stein (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 12/438,596

(22) PCT Filed: Sep. 5, 2007

(86) PCT No.: PCT/EP2007/007728
§ 371 (c)(1),
(2), (4) Date: Jun. 30, 2009

(87) PCT Pub. No.: WO2008/028640
PCT Pub. Date: Mar. 13, 2008

(65) Prior Publication Data
US 2010/0015433 A1 Jan. 21, 2010

(30) Foreign Application Priority Data

Sep. 6, 2006 (GB) .................................. 0617480.9

(51) Int. Cl.
| G02B 1/10 | (2015.01) |
| C08K 9/02 | (2006.01) |
| A61K 9/50 | (2006.01) |
| C08K 3/36 | (2006.01) |
| C08K 9/00 | (2006.01) |
| C09D 7/12 | (2006.01) |
| G02B 1/111 | (2015.01) |
| C08L 53/00 | (2006.01) |

(52) U.S. Cl.
CPC ............ *A61K 9/5089* (2013.01); *A61K 9/501* (2013.01); *C08K 3/36* (2013.01); *C08K 9/00* (2013.01); *C09D 7/1291* (2013.01); *G02B 1/111* (2013.01); *C08K 9/02* (2013.01); *C08K 2201/013* (2013.01); *C08L 53/00* (2013.01); *Y10T 428/254* (2015.01); *Y10T 428/2998* (2015.01)

(58) Field of Classification Search
None
See application file for complete search history.

(56) References Cited

U.S. PATENT DOCUMENTS

| 4,540,498 | A | 9/1985 | Wu et al. | |
| 5,100,471 | A | 3/1992 | Winnik et al. | |
| 6,685,966 | B1 | 2/2004 | Dominique et al. | |
| 7,138,161 | B2* | 11/2006 | Noguchi | 428/1.1 |
| 9,220,689 | B2 | 12/2015 | Armes et al. | |
| 2002/0068805 | A1 | 6/2002 | Futami et al. | |
| 2004/0135126 | A1* | 7/2004 | Schwark et al. | 252/500 |
| 2004/0249006 | A1* | 12/2004 | Gleason et al. | 521/61 |
| 2006/0078754 | A1* | 4/2006 | Murakami et al. | 428/532 |
| 2006/0172128 | A1* | 8/2006 | Shinohara | 428/212 |
| 2006/0181774 | A1* | 8/2006 | Ojima et al. | 359/586 |
| 2006/0269731 | A1 | 11/2006 | Yoshikawa et al. | |
| 2008/0241474 | A1 | 10/2008 | Kawai et al. | |

FOREIGN PATENT DOCUMENTS

| CN | 1631926 | | 6/2005 |
| CN | 101077792 | | 11/2007 |
| CN | 101184695 | | 5/2008 |
| CN | 101391199 | | 3/2009 |
| CN | 101611084 | | 12/2009 |
| EP | 1674891 | A1 * | 6/2006 |
| JP | 2001-247820 | | 9/2001 |
| JP | 2002-317152 | | 10/2002 |
| JP | 2004300172 | A * | 10/2004 |
| JP | 2005-28575 | | 2/2005 |
| JP | 2005-181543 | | 7/2005 |
| JP | 2006-126737 | | 5/2006 |
| JP | 2006-178041 | | 7/2006 |
| WO | WO 03/074026 | | 9/2003 |
| WO | WO 2004085493 | A1 * | 10/2004 |
| WO | WO 2004/096422 | | 11/2004 |
| WO | 2006/033456 | | 3/2006 |

OTHER PUBLICATIONS

Caruso, F.; Möhwald, H. Langmuir, 1999, 15 (23), pp. 8276-8281.*
Lu et al. (Synthesis and Crystallization of Hybrid Spherical Colloids Composed of Polystyrene Cores and Silica Shells, Langmuir 2004, 20, 3464-3470).*
Machine translation of 2004-300172A.*
Jang et al. (Synthesis and characterization of titania coated polystyrene spheres for electronic ink, Synthetic Metals 152, (2005) 9-12).*
Stein (Colloidal crystal templating of three-dimensionally ordered macroporous solids: materials for photonics and beyond, Current Opinion in Solid State and Materials Science 5 (2001) 553-564).*
Chen et al. (A Method for the Fabrication of Monodisperse Hollow Silica Spheres, Adv. Mater. 2006, 18, 801-806 (2006)).*
International Search Report for PCT/EP2007/007728, mailed Apr. 23, 2008.
Derwent Abstract AN 2005-521967/53, WPI Week 200553, Derwent Publications Ltd., London, GB; AN 2005-521967, XP002475930, JP 2005-181543A (Bridgestone Corp), Jul. 7, 2005.
Depasse, Interaction between silica and hydrophobic cations, 35 Brit. J. Indus. Med. 32, 32 (1978).
Lu et al, Synthesis and Crystallization of Hybrid Spherical Colloids Composed of Polystyrene Cores and Silica Shells, Langmuir 2004, 20, 3464-3470.
Caruso, Preparation and Characterization of Ordered Nanoparticle and Polymer Composite Multilayers on Colloids, Langmuir, vol. 15, 1999, pp. 8276-8281 (XP002376288).
U.S. Appl. No. 13/363,114, filed Jan. 31, 2012.
U.S. Appl. No. 12/676,084, filed Mar. 2, 2010.

(Continued)

*Primary Examiner* — Alexandre Ferre
(74) *Attorney, Agent, or Firm* — Nixon & Vanderhye P.C.

(57) ABSTRACT

The present invention relates to a composition suitable for forming an optical coating, the composition comprising core-shell nanoparticles, wherein said nanoparticles comprise: (a) core material comprising polymer; and (b) shell material comprising metal oxide.

23 Claims, No Drawings

(56) References Cited

OTHER PUBLICATIONS

Qun et al, *Recent Progress in pH/Temperature-Responsive Amphiphilic Block Copolymers*, Progress in Chemistry, vol. 18, No. 6 (Jun. 2006).
Preparation and Characterization of Polymer SiO2 Organic-Inorganic Nanocomposite Microspheres, Doct. Dissertation, Fudan University, Apr. 12, 2006.
Chen et al; *Preparation of hollow silica nanoparticles by surface-initiated atom transfer radical polymerization with polymeric latex as template*, Chemical Journal of Chinese Universities, vol. 26, No. 10, 1978-1980, Oct. 2005.
Liu et al; *Composite vacuoe structure nanoporous silica obtained by controlled synthesis using block copolymerization polypeptide*, Chinese Science Bulletin, vol. 51, No. 3, Feb. 2006.
Wang et al; *Preparation of Fluoro Emulsion Through Redox Initiator System, Paint & Coatings Industry*, vol. 35, No. 10, Oct. 2005.
Zenghui et al; *Preparatoin of Core-Shell Copolymer Emulsion of n-BMA/MMA, Paint & Coating Industry*, vol. 42, No. 2, Feb. 2012.
Yang, *Synthesis of Cationic Polyacrylamide*, Huanghuai Journal, vol. 12, No. 2, Jun. 1996.
Bütün et al; *Selective Quaternization of 2-(Dimethylamino)ethyl Methacrylate Residues in Tertiary Amine Methacrylate Diblock Copolymers*, Macromolecules 2001, 34, 1148-1159.
Bütün et al; *Synthesis and aqueous solution properties of near-monodisperse tertiary amine methacrylate homopolymers and diblock copolymers*, Polymer 42 (2001) 5993-6008.
Yao, Manuf and Appl Technique of Synthesis of the Polymer Emulsion, Ch. III, Advance in emulsion polymerization technique, ISBN 7-5019-2324-8 (1999).
WB Concrete Coatings, Performance, Formulations and Product Information, DSM Neoresins BV, Feb. 2013.
Xing et al; Basic Organic Chemistry. First volume, $3^{rd}$ ed., Higher Education Press, Jun. 2005.
Xing et al; *Organosilicon synthesis process and product application*, Chemical Industry Press, ISBN 7502502858-X, Sep. 2000.
Imhof, *Preparation and Characterization of Titani-Coated Polystyrene Spheres and Hollow Titania Shells*, Langmuir 2001, 17, 3579-3585.
Tissot et al, *Si-OH Functionalized Polystyrene Latexes. A step toward the Synthesis of Hollow Silica Nanoparticles*, Chem. Mater. 2002, 14, 1325-1331.
Xia et al, Dictionary of Chemical Technology, $4^{th}$ ed., Chemical Industry Press, ISBN 7-502502597-1 (2000).
Zhang, Handbook of Fine Chemical Raw Materials and Intermediates, Chemical Industry Press, ISBN 7-5025-6303-2 (2005).
Zhang et al; Advances in Macromolecular Materials, Chemical Industry Press, ISBN 7-502506956-1 (2005).
Polymer in NeoCryl XK-30, National Industrial Chemicals Notificatio and Assessment Scheme (NICNAS), File No.: LTD/1527, Jul. 2011.
CiHai, Editorial Board of CiHai, $1^{st}$ ed., Shanghai Lexicographical Publishing House, p. 266, Aug. 1980.
Kim et al; *Synthesis and Applications of TEOS/PDMS Hybrid Material by the Sol-gel Process*, Appl. Organometal. Chem. 13, 361-372 (1999).
Goodwin et al; *Studies on the preparation and characterization of monodisperse polystyrene lattices V: The preparation of cationic lattices*, Colloid & Polymer Sci. 257, 61-69 (1979).
Chen et al; *Preparation of Silica-Coated Polystyrene Hybrid Spherical Colloids*, Macromol. Chem. Phys. 2005, 206, 1896-1902.
Graf et al; *A general Method to Coat Colloidal Particles with Silica*, Langmuir 2003, 19, 6693-6700.
Ohtsuka et al; *Preparatoin and characterization of cationic opolymer latex. 2. Copolymerization of styrene with 4-vinylpyridine in an emulsifier-free aqueous medium*, Polymer, vol. 22, pp. 658-662, May 1981.

\* cited by examiner

CORE-SHELL NANOPARTICLES

This application is the U.S. national phase of International Application No. PCT/EP2007/007728, filed 5 Sep. 2007, which designated the U.S. and claims priority to Great Britain Application No. 0617480.9, filed 6 Sep. 2006, the entire contents of each of which are hereby incorporated by reference.

FIELD

The present invention is concerned with coatings comprising novel nanoparticles. More specifically, the invention relates to optical coatings comprising core-shell polymer-metaloxide or hollow metal oxide nanoparticles, methods for their preparation, and their potential application.

BACKGROUND AND SUMMARY

The use of nanoparticles to make optical coatings is known. Various optical functions can be achieved with such coatings. For example, an anti-reflective coating can be achieved by forming a porous coating with an effective refractive index lower than that of the substrate (U.S. Pat. No. 2,432,484). Typically these anti-reflective systems comprise a binder and nanoparticles. For example, U.S. Pat. No. 6,921,578 describes a method for preparing anti-reflective coating systems in which a binder (e.g. tetraethylorthosilicate TEOS) is hydrolyzed in the presence of the nanoparticles using an acid catalyst. While these approaches can lead to a coating with anti-reflective properties they suffer from a number of draw backs. For example, it can be difficult to make such coatings on an industrial scale as it is not easy to make stable coating compositions that result in coatings with reproducible optical and mechanical properties. Also, in order to produce coatings with suitable optical properties (such as refractive index) it is necessary to implement high levels of porosity. This can be achieved by incorporating voids in the binder which leads to a loss of mechanical properties.

It has been suggested to utilize hollow or porous particles in coatings (see, for example, EP1674891, US2004058177, WO2005021259, WO2005059601, WO2006030720, and WO2006033456). This places the void inside the particle rather than in the binder network resulting in an anti-reflective coating with better mechanical stability. Despite the apparent advantages of these hollow particle systems there are several drawbacks. For example, prior art hollow particles have proven difficult to control in terms of size and morphology. This makes it difficult to produce coatings having appropriate and reproducible properties. Also, the manufacture of such particles can be problematic, especially on an industrial scale. Furthermore, in certain cases a monodispersed system is desired which can be difficult to obtain with prior art methods. In addition, the means by which the void is created in the particle is not always compatible with its use in optical coatings.

Surprisingly it has been found that batches of polymer core-metal oxide shell particles can be produced in a reproducible manner and used in optical coatings such as anti-reflective coatings. These coatings show a better mechanical stability than coatings with comparable filled nanoparticles at the same level of reflection.

According to one aspect of the present invention, there is provided a composition suitable for forming an optical coating, the composition comprising core-shell nanoparticles, wherein said nanoparticles comprise:

(a) core material comprising polymer; and
(b) shell material comprising metal oxide.

In a particular embodiment of the invention there is provided a coating composition comprising core-shell nanoparticles, wherein said nanoparticles comprise:

(a) core material comprising polymer; and
(b) shell material comprising metal oxide, preferably silica, wherein said nanoparticles have a rod or worm-like morphology. In a specific embodiment, the polymer comprises a cationically stabilized co-polymer micelle—more preferably, a diblock or triblock copolymer. In another preferred embodiment, the polymer comprises a cationically stabilized latex.

According to a further aspect of the present invention, there is provided an optical coating wherein the coating comprises core-shell nanoparticles wherein the particles comprise core material comprising polymer and shell material comprising metal oxide.

According to a further aspect of the present invention, there is provided a process for forming an optical coating, the process comprising:

(a) applying a composition comprising core-shell nanoparticles to a substrate; and
(b) curing said composition to strengthen the network and remove the polymer core wherein the core-shell nanoparticles comprise core material comprising polymer and shell material comprising metal oxide.

According to a further aspect of the present invention, there is provided the use of core-shell nanoparticles for optical applications.

According to a further aspect of the present invention, there is provided a substrate at least partially coated with an optical coating composition comprising core-shell nanoparticles wherein the particles comprise core material comprising a polymer and shell material comprising metal oxide.

According to a further aspect of the present invention, there is provided an article comprising a substrate at least partially coated with an optical coating composition comprising core-shell nanoparticles wherein the particles comprise core material comprising a polymer and shell material comprising metal oxide.

According to a further aspect of the present invention, there is provided a thin-film coating comprising core-shell nanoparticles wherein the particles comprise core material comprising a polymer and shell material comprising metal oxide. As used herein, "thin-film" refers to coatings having an average thickness of 300 nm or less.

DETAILED DESCRIPTION

As used herein, the term "nanoparticles" refers to particles whose primary average particle size is less then 1 µm, preferably less than 500 nm, more preferably of less than 350 nm. Particle size can be measured by Dynamic Light Scattering (DLS) and Transmission Electron Microscopy (TEM).

As used herein, the term "core-shell" refers to particles comprising core material that comprises polymeric material (for example, homopolymers, random co-polymers, block-copolymers etc.) and shell material that comprises metal oxide (for example, silica, alumina, titania, tin oxide etc.).

As used herein, the term "binder" refers to a substance that can physically or chemically cross-link the nanoparticles and, preferably, also link the particles and substrate.

As used herein, the term "by weight of the solid fraction" refers to the weight percentage after removal of all solvent including water.

Unless otherwise stated all references herein are hereby incorporated by reference.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

The present invention relates to core-shell nanoparticles and their use in optical coatings. The particles of the present invention comprise a core comprising polymer and a shell comprising metal-oxide.

The nanoparticles for use in the present invention can be of any suitable size. Preferably the particles have an average specific size g where g=½×(length+width) of about 300 nm or less. More preferably the particles have an average size of about 200 nm or less. Even more preferably the particles have an average size of about 100 nm or less. Preferably the particles have an average size of 1 nm or more. More preferably the particles have an average size of about 10 nm or more.

Preferably the average specific size of the void is 1 nm or more, more preferably 3 nm or more, even more preferably 6 nm or more. Preferably the average specific size of the void is 100 nm or less, more preferably 80 nm or less, even more preferably 70 nm or less.

Preferably the shell is at least 1 nm thick, more preferably at least 5 nm, even more preferably at least 10 nm. Preferably the shell is 75 nm thick or less, more preferably 50 nm or less, even more preferably 25 nm or less.

The nanoparticles may comprise a mixture of different types, sizes, and shapes of particles. However, preferably the nanoparticles are relatively monodispersed, that is of a reasonably uniform size and shape.

In one embodiment the particles used herein are non-spherical such as, preferably, rod-like or worm-like particles. In another preferred embodiment the particles are substantially spherical.

In a preferred embodiment the void fraction is preferably from about 5% to about 90%, more preferably from about 10% to about 70%, even more preferably from about 25% to about 50%. The void fraction (x) may be calculated according to the following equation:

$$x=(4\pi r_a^3/3) \div (4\pi r_b^3/3) \times 100$$

wherein $r_a$ is the radius of the core and $r_b$ is the radius of the outer shell.

The nanoparticles for use herein comprise a core material which comprises a polymer. Any suitable polymer may be used such as, for example, homopolymers, random co-polymers, block-copolymers, diblock-copolymers, triblock-copolymers, and combinations thereof.

Preferably the core comprises about 30% or more, more preferably about 50% or more, even more preferably about 70% or more, even more preferably still about 90% or more, by weight, of polymer.

In the present invention it may be required to remove some or all of the core material from the particle. This may be achieved in any suitable manner at any suitable point in the production process. Preferred methods include, for example, thermodegradation, photodegradation, solvent washing, electron-beam, laser, catalytic decomposition, and combinations thereof. Preferably the core is removed after the nanoparticles has been added to a coating or a composition that is used in forming a coating. Therefore, the scope of the present invention encompasses optical coatings comprising core-shell nanoparticles where the core is present and where the core has been partially or fully removed.

In a preferred embodiment the core comprises thermodegradable or thermo-labile polymer. Preferred polymers are those which become labile at 600° C. or less, more preferably 450° C. or less, even more preferably 350° C. or less. Preferably the polymers become labile at room temperature or higher, more preferably 150° C. or higher, even more preferably 250° C. or higher. Examples of suitable heat-labile polymers include homopolymers, random co-polymers, block-copolymers, diblock-copolymers, triblock-copolymers, and combinations thereof.

Preferably the core comprises a polymer selected from polyesters, polyamides, polycarbonates, polyurethanes, polystyrenes, poly(meth)acrylates, polymethacrylates, and combinations thereof.

Preferably the core comprises an poly(meth)acrylate. A poly(meth)acrylate is understood to be a (co)polymer of one or more vinyl monomers. Examples of suitable (non (permanent) quaternisable) monomers include: styrenes, such as styrene itself, .alpha.-methlystyrene, o-, m- and p-methylstyrene, o-, m- and p-ethylstyrene, p-chlorostyrene and p-bromostyrene; normal and branched acrylic and methacrylic esters of alkanols (usually C1-C12) and cycloalkanols (usually C5-C12) such as methyl methacrylate, ethyl methacrylate, n-butyl methacrylate, t-butyl methacrylate, 2-ethylhexyl methacrylate, isobornyl methacrylate and cyclohexyl methacrylate and the corresponding acrylates; vinyl esters such as vinyl acetate and vinyl alkanoates; vinyl halides such as vinyl chloride; vinylidene halides such as vinylidene chloride; dienes such as 1,3-butadiene and isoprene.

A functional monomer(s) e.g. for imparting crosslinkability may optionally be included, examples of which include hydroxy and epoxy functional (meth)acrylates such as hydroxyalkyl (usually C1-C12) methacrylate e.g. 2-hydroxyethyl methacrylate, glycidyl methacrylate, and the corresponding acrylates, as well as keto- and aldehyde-functional monomers such as acrolein, methacrolein and methyl vinyl ketone, acetoacetoxy esters of hydroxyalkyl (usually C1-C12) acrylates and methacrylates such as acetoacetoxyethyl acrylate and methacrylate, and also keto or aldehyde-containing amides such as diacetone acrylamide. Examples of tertiary amine functional monomers include: vinyl monomers bearing non-ionic amine functional groups (component i), (a)), which are used to form the oligomer include but are not limited to N,N-dimethylaminoethyl (meth)acrylate, N,N-dimethylaminohexyl (meth) acrylate, N,N-diethylaminoethyl (meth)acrylate, N-methyl-N-butyl-aminoethyl (meth)acrylate, tert-butylaminoethyl (meth)acrylate, N,N-dimethylaminopropyl (meth)acrylate, 2-(1,1,3,3-tetramethylbutylamino) ethyl (meth)acrylate, beta-morpholinoethyl (meth)acrylate, 4-(beta-acryloxyethyl) pyridine, vinylbenzylamines, vinylphenylamines, 2-vinylpyridines or 4-vinylpyridines, p-aminostyrenes, dialkyaminostyrenes such as N,N-diaminomethylstyrene, substituted diallylamines, N-vinylpiperidines, N-vinylimidazole, N-vinylimidazoline, N-vinylpyrazole, N-vinylindole, (meth)acryl amide like 2-(dimethylamino)ethyl (meth) acrylamide, 2-(tert-butylamino)ethyl (meth)acrylamide, 3-(dimethylamino)propyl (meth)acrylamide, N-substituted (meth)acryl amides, N-aminoalkyl (meth)acrylamides, vinyl ethers like 10-aminodecyl vinyl ether, 9-aminooctyl vinyl ether, 6-(diethylamino)hexyl vinyl ether, 5-aminopentyl vinyl ether, 3-aminopropyl vinyl ether, 2-aminoethyl vinyl ether, 2-aminobutyl vinyl ether, 4-aminobutyl vinyl ether, 2-dimethylaminoethyl vinyl ether, N-(3,5,5-triethylhexyl) aminoethyl vinyl ether, N-cyclohexylaminoethyl vinyl ether, N-tert-butylaminoethyl vinyl ether, N-methylaminoethyl vinyl ether, N-2-ethylhexylaminoethyl vinyl ether, N-tert-octylaminoethyl vinyl ether, beta-pyrrolidinoethyl vinyl ether, or (N-beta-hydroxyethyl-N-methyl) aminoethyl vinyl ether may also be used. Cyclic ureido or thiourea containing unsaturated monomers like (meth)acryloxyethyl ethyleneurea, (meth)acryloxyethyl ethylenethiourea (meth)acrylamide ethyleneurea, (meth)acrylamide ethylenethiourea and alike can also be used. Mixtures of amine functional vinyl monomers can also be used. If desired these non-ionic monomers may be made cationic by, for example, neutralisation as described below.

Examples of vinyl monomers bearing permanent quaternary ammonium functional groups (component i), (b)), which are used to form the oligomer are methacrylamidopropyl trimethylammonium chloride (MAPTAC), diallyl dimethyl ammonium chloride (DADMAC), 2-trimethyl ammonium ethyl methacrylic chloride (TMAEMC) and quartenary ammonium salts of substituted (meth)acrylic and (meth)acrylamido monomers. For the amine functional vinyl monomers that are already cationic, such as the examples of vinyl monomers bearing permanent quaternary ammonium functional groups listed above, neutralisation is not required.

The vinyl monomers bearing already neutralised amine functional groups (component i), (c)), which may used to form the vinyl oligomer are the same as the vinyl monomers bearing non-ionic amine functional groups listed above for component i), a). However, to obtain monomer (c), monomer (a) is treated with acids, preferably with organic acids, prior to being polymerised. In this way the non-ionic amine functional monomers are made cationic prior to polymerisation. This can be done with all or part of the non-ionic amine functional vinyl monomers.

Mixtures of amine functional vinyl monomers that need to be neutralised and permanent quaternary ammonium functional monomers that are already cationic can also be used.

Preferably the amine functional vinyl monomers are selected from the group consisting of dimethylaminoethyl (meth)acrylate, diethylaminoethyl (meth)acrylate, tert-butylaminoethyl (meth)acrylate, dimethylaminopropyl (meth) acrylate and mixtures thereof. More preferred is dimethylaminoethyl (meth)acrylate.

Preferably the core comprises a polymer selected from block copolymers, more preferably diblock and/or triblock copolymers.

In a preferred embodiment the core material comprises cationic polymer. More preferably cationic block copolymer. Even more preferably still a diblock copolymer micelle. Said diblock copolymer micelle preferably has a core comprising at least one block of a first polymer and a corona comprising at least one block of a second polymer, wherein said second polymer is different to said first polymer.

Preferably, said copolymer comprises a first polymer and a second polymer which both comprise amino-based (alk) acrylate monomer units, more preferably tertiary amino-based (alk)acrylate units, most preferably tertiary aminoalkyl (alk)acrylate units. Particularly preferably, said (alk) acrylate units comprise acrylate or, more particularly, methacrylate units.

In preferred embodiments, said tertiary aminoalkyl methacrylate units comprise dialkylaminoalkyl methacrylate units, especially dialkylaminoethyl methacrylate units. In a particularly preferred embodiment, said copolymer comprises poly[2-(diisopropylamino)ethyl methacrylate)-block-2-(dimethylamino)ethyl methacrylate] (PDPA-PDMA).

The micelles may be non-crosslinked or crosslinked (such as shell-crosslinked) micelles based on said polymers. Thus, especially preferred embodiments envisage non-crosslinked or shell crosslinked micelles based on tertiary amine methacrylate-derived block copolymers such as poly[2-(diisopropylamino)ethyl methacrylate)-block-2-(dimethylamino) ethyl methacrylate].

One possible way of crosslinking of the micelles of said tertiary amino-based (alk)acrylate copolymers is by partially or fully quaternising the tertiary amino groups of said copolymers with bifunctional quaternising agents. Thus, in the case of a preferred embodiment, partial crosslinking of poly[2-(diisopropylamino)ethyl methacrylate)-block-2-(dimethylamino)ethyl methacrylate] (PDPA-PDMA) may be achieved by selective quaternisation/crosslinking of the PDMA chains with a suitable bifunctional quaternising agent, for example a bis(haloalkoxy)alkane, such as 1,2-bis-(iodoethoxy)ethane (BIEE). In this preferred embodiment, the PDPA chains remain essentially unquaternised.

The invention also envisages analogous non-crosslinked quaternised derivatives, wherein quaternisation is achieved by means of monofunctional quaternising agents, such as alkyl halides, in particular alkyl iodides such as iodomethane. However, it is believed that control of the silica deposition process may be enhanced in the case of crosslinked materials.

The degree of polymerisation of the polymer is preferably controlled within specified limits. In a preferred embodiment of the invention, the degree of polymerisation of the PDPA-PDMA copolymer is preferably controlled such that the mean degree of polymerisation of the PDPA falls in the range of 20-25 and the mean degree of polymerisation of the PDMA falls in the range of 65-70, with particularly favourable results having been obtained with the $PDPA_{23}$-$PDMA_{68}$ copolymer, wherein the subscripts denote the mean degrees of polymerisation of each block. In the said embodiment, PDPA units form the cores of the micelles and PDMA units form the coronas of the micelles.

The polymeric core material may be prepared by any suitable polymerisation technique, but for preferred embodiments particularly favourable results were achieved when employing methods such as group transfer polymerisation and controlled radical polymerization techniques like RAFT and ATRP. The core material is then coated with metal oxide by, for example, treatment with a suitable precursor.

In a preferred embodiment the polymeric core is a latex, more preferably ionically stabilized polymer latex. As used herein, the term 'latex' refers to stabilized suspension of polymeric particles. Preferably the suspension is a cationic suspension. Preferably the average size of the polymeric particles is in the range 1-400 nm, more preferably 10-250 nm, even more preferably 30-150 nm. Preferably the pH range of the suspension is from 3 to 7, more preferably from 3.5 to 6.

Preferably the latex comprises polymer and cationic surfactant. Any suitable polymer may be used such as, for example, homopolymers, random copolymers, block-copolymers, diblock-copolymers, triblock-copolymers, and combinations thereof.

Preferably, the polymer comprises styrene monomers, (meth)acrylic monomers, and copolymers and combinations thereof.

Preferably, the surfactant comprises ammonium surfactant.

The core preferably comprises an aqueous cationic vinyl polymer composition. The cationic group may be incorporated in to the polymer or may be added in any other form such as, for example, by the addition of a cationic surfactant. Preferably the cationic groups are at least partially bound to the polymer. Preferably the cationic groups are incorporated into the polymer during polymerisation.

The polymer may be made in any suitable many. For example, in solution, dispersed and optionally solvent evaporated; with surfactant; with an polymeric (or oligomeric) stabilizer optionally with low levels of surfactant being present; by bulk or suspension polymerization, followed by dissipation of this polymer in water optionally followed by a further polymerization step. In a particular embodiment, a polymer dispersion (or solution) A is used as stabilizer for further vinyl polymerizations. Polymer A can for instance be a polyurethane, a polyester, polyamide, polycarbonate etc.

The nanoparticles of the present invention comprise shell material which comprises metal oxide. Any suitable metal oxide may be used. Preferably the metal oxide is selected from titanium dioxide, zirconium oxide, antimony doped tin oxide, tin oxide, aluminium oxide, silicon dioxide, and combinations thereof.

Preferably the shell comprises silica. More preferably the shell comprises at least 90%, by weight, of silica.

Preferably, said shell material comprises silica which is deposited on said core material from at least one silica precursor. Optionally, said at least one silica precursor may comprise an inorganic silicate, for example an alkali metal silicate, such as sodium silicate. However, preferred silica precursors comprise organosilicate compounds, especially alkyl silicates such as tetramethyl orthosilicate or tetraethyl orthosilicate. Most preferably, said silica precursor comprises tetramethyl orthosilicate. Said treatment is found to effectively crosslink the copolymer chains in uncrosslinked micelles, and thereby stabilise the micelles towards dissociation.

Deposition of silica may be carried out by simply treating the polymers with suitable silica precursors under mild conditions. Thus, both in the case of the preferred copolymer and latex micelles, these materials may be stirred with a silica precursor, typically an organosilicate compound, especially an alkyl silicate such as tetraethyl orthosilicate or, most preferably, tetramethyl orthosilicate, for between 10 and 300 minutes at 5-60° C. and a pH of between 6.2 and 9.0. In a typical reaction, PDPA-PDMA copolymer micelles may be treated with tetramethyl orthosilicate for 20 minutes at 20° C. and pH 7.2. The method of the second aspect of the present invention does, in this regard, offer significant advantages over the methods of the prior art, which require that silica deposition procedures should be carried out at low pH values, and typically at pH 1.

Particularly favourable results have been achieved with compositions based on selectively quaternised non-cross-linked and shell crosslinked (SCL) micelles derived from tertiary amine methacrylate-based block copolymers, a specific example being poly[2-(diisopropylamino)ethyl methacrylate)-block-2-(dimethylamino)ethyl methacrylate] (PDPA-PDMA), and such materials have proved to be particularly successful when used as templates for the biomimetic formation of well-defined copolymer-silica nanoparticles of less than 50 nm diameter. Diblock copolymer micelles comprising either partially or fully quaternised poly(2-(dimethylamino)ethyl methacrylate) (PDMA) coronas and hydrophobic poly(2-(diisopropylamino)ethyl methacrylate) (PDPA) cores in particular have been used as nano-sized templates for the deposition of silica from aqueous solution under mild conditions, i.e. at pH 7.2 and 20° C.

Furthermore, favourable results have been achieved with compositions comprising acrylic copolymer latex particles (e.g. NeoCryl XK-30 available from DSM NeoResins). Preferred latex particles have an average particle size of from 60 to 90 nm and are stabilized with a cationic surfactant. These particles have been used as templates for silica deposition. The biomimetic deposition of silica can be performed using TMOS as precursor in a neutral aqueous environment at room temperature.

The fact that mild conditions, fast reaction times, and accessible reagents can be utilised herein may offer clear advantages when preparing commercially applicable processes. In addition, the ability to control the size and/or properties of the particles offers benefits.

Coating compositions herein typically comprise a binder. The primary function of the binder is to keep the integrity of the coating intact. That is, to fix the nanoparticles in the coating and to the substrate. Any suitable binder may be used but preferably the binder forms covalent bonds with the particles and the substrate. The binder—before curing—preferably comprises inorganic compounds with alkyl or alkoxy groups. Further, the binder preferably polymerises itself to form a substantially continuous polymeric network.

In one embodiment of the invention the binder comprises an inorganic material. Preferably the binder consists substantially of an inorganic material. The binder preferably comprises compounds derived from one or more inorganic oxides. Preferably the binder comprises hydrolysable material such as metal-alkoxides. Preferably the binder comprises alkoxy silanes, alkoxy zirconates, alkoxy aluminates, alkoxy titanates, alkyl silicates, sodium silicates, or a combination thereof. Preferred are alkoxy silanes, preferably tri- and tetra-alkoxy silanes. Preferably, ethyl silicate, aluminate, zirconate, and/or titanate binders are used. Tetra alkoxy silane is most preferred.

The amount of binder in the coating composition is preferably 1% or more, more preferably 2% or more, by weight of the solid fraction. Preferably the amount of binder will be 40% or less, more preferably 25% or less, by weight of the solid fraction. The percentage is calculated as the amount of metal oxide in the binder relative to the amount of metal oxide in the nanoparticles.

Preferably the pH of the mixture of binder and nanoparticles is about 2 or higher, more preferred about 3 or higher. The pH is preferably about 7 or lower, more preferred about 4 or lower.

The compositions herein may comprise a solvent. Preferred solvent include water, organic solvents, and combinations thereof. However, depending on the chemistry of the binder, many solvents are useful. Suitable solvents include, but are not limited to, water, non-protic organic solvents, alcohols, and combinations thereof. Examples of suitable solvents include, but are not limited to, isopropanol, ethanol, acetone, ethylcellosolve, methanol, propanol, butanol, ethyleneglycol, propyleneglycol, methyl-ethyl-ether, methyl-butyl-ether, toluene, methyl-ethylketone, and combinations thereof.

Generally, the coating composition comprises an amount of non-reactive solvent to adjust the viscosity of the particles and binder to such a value that thin layers can be applied to the substrate. Preferably, the viscosity will be about 2.0 mPa·s or more, preferably 2.2 mPa·s or more, even more preferably about 2.4 mPa·s or more. Preferably, the viscosity is about 20 mPa·s or less, preferably about 10 mPa·s or less, more preferably about 6 mPa·s or less, and even more preferably about 3 mPa·s or less. The viscosity can be measured with a Ubbelohde PSL ASTM IP no 1 (type 27042).

Preferably, before curing, the amount of solids in the coating compositions herein is about 5% by weight or less, more preferably about 4%, by weight, or less, even more preferred about 3%, by weight, or less. Preferably the amount of solids is about 0.5%, by weight, or more, more preferably about 1%, by weight, or more, more preferably about 1.5%, by weight, or more.

The present compositions are suitable for forming optical coatings. As used herein, the term "optical coatings" refers to coatings with an optical function as major functionality. Examples of optical coatings include those designed for anti-reflective, anti-glare, anti-dazzle, anti-static, EM-control (e.g. UV-control, solar-control, IR-control, RF-control etc.) functionalities.

Preferably the present coatings are anti-reflective. More preferably the present coatings are such that, when measured for one coated side at a wavelength between 425 and 675 nm (the visible light region), the minimum reflection is about 2% or less, preferably about 1.5% or less, more preferably about 1% or less. The average reflection at one side, over the region of 425 to 675 nm will preferably be about 2.5% or less, more preferably about 2% or less, even more preferably about 1.5% or less, still more preferably about 1% or less. Generally, the minimum in the reflection will be at a wavelength between 425 and 650 nm, preferably at a wavelength of 450 nm or higher, and more preferably at 500 nm or higher. Preferably, minimum is at a wavelength of 600 nm or lower. The optimal wavelength for the human eye is a minimum reflection around 550 nm as this is the wavelength (colour) at which the human eye is most sensitive.

The coating composition can be applied to a substrate. Any suitable substrate may be used. Preferred are substrates that may benefit from an optical coating especially those that would benefit from an anti-reflective coating. The substrate preferably has a high transparency. Preferably the transparency is about 94% or higher at 2 mm thickness and at wavelength between 425 and 675 nm, more preferably about 96% or higher, even more preferably about 97% or higher, even more preferably about 98% or higher.

The substrate herein may be organic. For example, the substrate may be an organic polymeric such as polyethylene naphthalate (PEN), polycarbonate or polymethylmethacrylate (PMMA), polyester, or polymeric material with similar optical properties. In this embodiment, it is preferred to use a coating that can be cured at temperatures sufficiently low that the organic substrate material remains substantially in its shape and does not suffer substantially due to thermal degradation. One preferred method is to use a catalyst as described in EP-A-1591804. Another preferred method of cure is described in WO 2005/049757.

The substrate herein may be inorganic. Preferred inorganic substrates include ceramics, cermets, glass, quartz, or combinations thereof. Preferred is float glass. Most preferred is low-iron glass, so-called white glass, of a transparency of 98% or higher.

Preferably the coating composition is applied to the article so that the resultant dry coating thickness is about 50 nm or greater, preferably about 70 nm or greater, more preferably about 90 nm or greater. Preferably the dry coating thickness is about 300 nm or less, more preferably about 200 nm or less, even more preferably about 160 nm or less, still more preferably about 140 nm or less.

A number of methods are available to apply thin coatings on substrates. Any method of applying a wet coating composition suitable for obtaining the required thickness would be acceptable. Preferred methods include meniscus (kiss) coating, spray coating, roll coating, spin coating, and dip coating. Dip coating is preferred, as it provides a coating on all sides of the substrate that is immersed, and gives a repeatable and constant thickness. Spin coating can easily be used if smaller glass plates are used, such as ones with 20 cm or less in width or length. Meniscus, roll, and spray coating is useful for continuous processes.

Once applied to the substrate the coating may require curing or hardening. If required the curing may be carried out by any suitable means which is often determined by the type of binder material used. Examples of means of curing include heating, IR treatment, exposure to UV radiation, catalytic curing, and combinations thereof.

If a catalyst is used it is preferably an acid catalyst. Suitable catalysts include, but are not limited to, organic acids like acetic acid, formic acid, nitric acid, citric acid, tartaric acid, inorganic acids like phosphoric acid, hydrochloric acid, sulphuric acid, and mixtures thereof, although acid with buffer capacity are preferred.

In a preferred embodiment the curing is achieved by heating. Heat curing is generally carried out at about 150° C. or more, preferably about 200° C. or more. Preferably, the temperature will be about 700° C. or less, more preferably about 500° C. or less. Curing generally takes place in 30 seconds or more. Generally, curing is performed in 10 hours or less, preferably 4 hour or less.

In one embodiment, the coating composition is heat-curable and is applied to a glass plate before a tempering step of said plate. The tempering step is usually carried out at temperature of up to 600° C. In this case the curing and tempering process are thus carried out in one step.

Preferably the core material of the nanoparticles is also at least partially, more preferably substantially fully, degraded by the curing step.

Preferably the substrate is cleaned before the coating is applied. Small amounts of contaminants such as dust, grease and other organic compounds cause the coatings to show defects.

It has been found that the coatings according to the present invention show good optical and mechanical properties. Desirable mechanical properties include good adhesion to the substrate, good puncture resistance, good scratch resistance, and good wear resistance.

The invention will now be further illustrated, though without in any way limiting the scope of the disclosure, by reference to the following examples.

EXAMPLES

Example 1

$PDPA_{23}$-$PDMA_{68}$ diblock copolymer was synthesised by sequential monomer addition using group transfer polymerisation according to the methods described in 'Bütün, V.; Armes, S. P.; Billingham, N. C. *Chem. Commun.* 1997, 671-672'. Gel permeation chromatography analysis indicated an $M_n$ of 18,000 and an $M_w/M_n$ of 1.08 using a series of near-monodisperse poly(methyl methacrylate) calibration standards. The mean degrees of polymerisation of the PDPA and PDMA blocks were estimated to be 23 and 68, respectively, using $^1$H NMR spectroscopy.

Non-crosslinked micelles of the $PDPA_{23}$-$PDMA_{68}$ diblock copolymer (degree of quaternisation=0%) were prepared by molecular dissolution at pH 2, followed by adjusting the solution pH to pH 7.2 using NaOH. Dynamic light scattering (DLS) studies at 25° C. indicated an intensity-average micelle diameter of 37 nm for a 0.25 wt. % copolymer micelle solution at pH 7.2.

Silicification of the said micelles was achieved by mixing 2.0 ml of an aqueous micelle solution (0.25 w/v % at pH 7.2) with 1.0 ml tetramethyl orthosilicate, and then stirring the initially heterogeneous solution under ambient conditions for 20 minutes. The hybrid core-shell copolymer-silica nanoparticles thus obtained were washed with ethanol, then subjected to three centrifugation/redispersion cycles at 16,000 rpm for 5 minutes. Redispersal of the sedimented core-shell copolymer-silica nanoparticles was subsequently achieved with the aid of an ultrasonic bath.

Example 2

$PDPA_{23}$-$PDMA_{68}$ diblock copolymer was synthesised by sequential monomer addition using group transfer polymerisation as in Example 1.

Partial quaternisation of the PDMA block (targeting a degree of quaternisation of either 50% or 100%) using iodomethane was conducted in THF for 24 hours, as described in 'Bütün, V.; Armes, S. P.; Billingham N. C. *Macromolecules* 2001, 34, 1148-1159'.

Non-crosslinked micelles prepared using either 50% or 100% quaternised $PDPA_{23}$-$PDMA_{68}$ diblock copolymers were also prepared by pH adjustment, as described in Example 1. DLS studies conducted at pH 7.2 indicated intensity-average diameters of 29 nm and 26 nm for 0.25 wt. % aqueous solutions of 50% and 100% quaternised copolymer micelles, respectively.

Tetramethyl orthosilicate (1.0 ml) was added at 20° C. to 2.0 ml of a 0.25 wt. % aqueous solution of $PDPA_{23}$-$PDMA_{68}$ copolymer micelles in which the PDMA chains were 50% quaternised, and silica deposition was allowed to continue for 20 minutes, with continuous stirring, prior to isolation via centrifugation.

DLS studies on the hybrid core-shell copolymer-silica nanoparticles obtained using the 50% quaternised copolymer precursor indicated an intensity-average micelle diameter of 34 nm at around pH 7.

Example 3

$PDPA_{23}$-$PDMA_{68}$ diblock copolymer was synthesised by sequential monomer addition using group transfer polymerisation, and non-crosslinked micelles of the $PDPA_{23}$-$PDMA_{68}$ diblock copolymer were prepared as described in Example 1.

Shell crosslinking of the coronal PDMA chains was achieved by adding a bifunctional quaternising agent, 1,2-bis-(2-iodoethoxy)ethane (BIEE, 0.15 moles per DMA residue for a target degree of cross-linking of 30%) to a 0.25% $PDPA_{23}$-$PDMA_{68}$ copolymer micelle solution at pH 7.2. Shell crosslinking was carried out at 25° C. for at least 72 hours. After shell crosslinking, DLS studies indicated an intensity-average diameter of 32 nm and TEM studies suggested a number-average diameter of 26 nm for the dried SCL micelles. On adjusting the aqueous SCL micelle solution to pH 2, DLS studies indicated an intensity-average diameter of 45 nm due to swelling of the SCL micelles.

This DLS experiment also confirmed successful shell crosslinking, since the non-crosslinked micelles simply dissociate at low pH to form a molecular solution, because the PDPA chains are highly protonated, and hence no longer hydrophobic, at low pH. In addition, SCL micelles prepared using the 50% quaternised copolymer had an intensity-average diameter of 37 nm at pH 7.2 as indicated by DLS.

Silica deposition was achieved by adding a 2.0 ml aliquot of a 0.25 wt. % SCL micelle solution to a mixture of 2.0 ml methanol and 2.0 ml tetramethyl orthosilicate, wherein the methanol acted as a co-solvent and ensured that the TMOS was miscible with the aqueous phase. After continuing silica deposition for 40 minutes, TEM studies of the obtained product confirmed the formation of well-defined core-shell copolymer-silica nanoparticles. Even after continuing the treatment for 120 minutes, however, no evidence for non-templated silica nanostructures was observed.

Example 4

$PEO_{45}$-$PDMA_{29}$-$PDPA_{76}$ triblock copolymer was synthesized by Atom Transfer Radical Polymerisation using a PEO-based macro-initiator by firstly adding the macro-initiator (1.00 g, 0.463 mmol) to a 25 ml one-neck flask, then degassing by three vacuum/nitrogen cycles, followed by the addition of DMA (2.18 g, 13.88 mmol, target DP 30), 2,2'-bipyridine (144.5 mg, 0.925 mmol) and then 3.2 ml of a degassed 95/5 v/v IPA/water mixture. The solution was placed in a 40° C. oil bath and stirred until homogeneous. Copper(I) chloride (45.8 mg, 0.463 mmol) was then added and the reaction was carried out at 40° C. for 3.5 hours under nitrogen with continual stirring. After this time, the DMA monomer conversion reached 96%, as determined by $^1$H NMR spectroscopy.

Thereafter, a mixture of DPA (4.94 g, 23.13 mmol, target DP=50) and 5.0 ml of a 95/5 v/v IPA/water mixture was added. The second-stage polymerization was carried out at 40° C. for 18.5 hours, before being terminated by exposure to air. $^1$H NMR analysis showed that the DPA monomer conversion reached 99%. The copolymer solution was diluted with THF (200 ml) and passed through a silica column to remove the spent catalyst. The copolymer solution was then concentrated under vacuum and the solid copolymer was precipitated into deionized water (100 ml) to remove residual monomer and any unreacted PEO-DMA diblock copolymer. The purified white copolymer was isolated by freeze-drying under vacuum overnight to give an overall yield of 6.1 g (76%).

The micellar rods formed by the $PEO_{45}$-$PDMA_{29}$-$PDPA_{76}$ triblock copolymer were prepared by molecular dissolution at pH 2, followed by adjusting the solution pH to 7.2 using NaOH. The final copolymer concentration was 1.0 wt. %. Silica deposition was achieved by adding excess TMOS (0.20 g; i.e. a TMOS:copolymer mass ratio of 20:1) to 1.0 ml of copolymer solution and silicification was then conducted for 20 minutes at 20° C. and pH 7.2. Silica rods were obtained by washing with ethanol, followed by three centrifugation/redispersion cycles at 13,000 rpm for 15 minutes.

Example 5

For the preparation of pre-oligomerised tetraethoxysilane, water (53.6 g, 12.2 wt-%) and acetic acid (5.9 g) were added to a stirred solution of tetraethoxysilane (58.4 g) in 2-propanol (159.0 g). After 24 h, the mixture was diluted with 2-propanol (160.7 g) to the desired concentration. The pH value of the resulting mixture was lowered to 1.0 by addition of concentrated nitric acid (1.3 g)

To a 5.7-wt % suspension of silica core-shell particles (125 mg), as prepared in Example 2,2-propanol (125 mg) was added. Then, various amounts of the pre-oligomerised tetraethoxysilane was added and the mixture was shaken for 5 min. The resulting formulation was spin-coated onto cleaned glass plates of a size of 5 cm×1 cm with a speed of 2500 min$^{-1}$. The AR film was applied on both sides of the glass substrate. The coated glass plate was cured at a temperature of 450° C. for 4 hours.

Samples had a reflection of 1.3% and were not visually damaged by the steel wool test (250 g loading). Samples prepared in a similar manner using filled silica particles having similar dimensions to the core-shell particles showed a reflection of 1.9% and higher.

Example 6

NeoCryl XK-30 (4.41 g, 42.5% acrylic copolymer available from DSM NeoResins) was treated with water (10.00 g). Then, tetramethoxysilane (10.00 ml) was added over a period of 2 hours at room temperature. After complete addition, the mixture was stirred for 1.5 h at room temperature and subsequently diluted with ethanol (108.4 g).

A 3.1 wt-% suspension of these particles was dip-coated onto cleaned glass plates of a size of 8 cm×10 cm using a withdrawal speed of 4.2 mm·s$^{-1}$. The AR film was applied on both sides of the glass substrate. The coated glass plate was cured at a temperature of 450° C. for 4 h. The reflection at 550 nm was less than 1.

The invention claimed is:

1. A process for forming an anti-reflective coating on a substrate, the process comprising:
   (i) providing a coating composition comprising core-shell nanoparticles, wherein the nanoparticles have an average size of 10-200 nm and comprise (a) a core material which is thermo-labile at a temperature of 150° C. to 600° C., the core material comprising a cationic vinyl copolymer composition comprised of a polymer selected from the group consisting of poly(meth)acrylate and copolymers thereof having cationic groups incorporated therein during polymerization; and (b) a shell material comprising metal oxide deposited onto the cationic vinyl copolymer composition;
   (ii) applying the coating composition to a substrate to thereby obtain an applied coating;
   (iii) curing the applied coating; and
   (iv) subjecting the applied coating to an elevated temperature of at least 150° C. sufficient to remove some or all of the core material from the core-shell nanoparticles in the applied coating.

2. The process according to claim 1, wherein steps (iii) and (iv) are carried out simultaneously.

3. The process according to claim 2, wherein steps (iii) and (iv) are practiced by heating the applied coating to cause the core material to be at least partially thermally degraded.

4. The process according to claim 3, wherein the substrate is inorganic and wherein curing is carried out at 200-700° C.

5. The process according to claim 1, wherein the resulting coating has a thickness of 50-300 nm.

6. The process according to claim 1, wherein the polymer is selected from latexes, diblock-copolymers, triblock copolymers, and combinations thereof.

7. The process according to claim 1, wherein metal oxide is silica.

8. The process according to claim 1, wherein the composition comprises binder.

9. The process according to claim 1, wherein the composition comprises a binder comprising inorganic material.

10. The process according to claim 1, wherein the nanoparticles have a potential void fraction, resulting from partially or fully removing the core material from the nanoparticle, of 5% to 90%.

11. A substrate at least partially provided with an anti-reflective coating as obtained with the process according to claim 1.

12. The process according to claim 1, wherein steps (iv) and (v) are practiced simultaneously by subject the coating composition to a temperature of from 150° C. to 600° C.

13. A process for forming an anti-reflective coating on a substrate, the process comprising:
   (i) forming core-shell nanoparticles having an average size of 10-200 nm by depositing a shell material comprising silica onto a core material which is thermo-labile at a temperature of 150° C. to 600° C. and comprises a cationic vinyl copolymer composition comprised of a polymer selected from the group consisting of poly(meth)acrylate and copolymers thereof having cationic groups incorporated thereinto during polymerization;
   (ii) forming a coating composition comprising the core-shell nanoparticles;
   (iii) applying the coating composition to a substrate to thereby obtain an applied coating;
   (iv) curing the applied coating; and
   (v) subjecting the applied coating to an elevated temperature of at least 150° C. sufficient to remove some or all of the core material from the core-shell nanoparticles in the applied coating.

14. The process according to claim 13, wherein steps (iv) and (v) are carried out simultaneously.

15. The process according to claim 14, wherein steps (iv) and (v) are practiced by heating the applied coating to cause the core material to be at least partially thermally degraded.

16. The process according to claim 15, wherein the substrate is inorganic and wherein curing is carried out at 200-700° C.

17. The process according to claim 13, wherein the resulting coating has a thickness of 50-300 nm.

18. The process according to claim 13, wherein the polymer is selected from latexes, diblock-copolymers, triblock copolymers, and combinations thereof.

19. The process according to claim 13, wherein the composition comprises binder.

20. The process according to claim 13, wherein the composition comprises a binder comprising inorganic material.

21. The process according to claim 13, wherein the nanoparticles have a potential void fraction, resulting from partially or fully removing the core material from the nanoparticle, of 5% to 90%.

22. A substrate at least partially provided with an anti-reflective coating as obtained with the process according to claim 13.

23. The process according to claim 13, wherein steps (iv) and (v) are practiced simultaneously by subject the coating composition to a temperature of from 150° C. to 600° C.

* * * * *